United States Patent
Sheldon (12)

(10) Patent No.: US 6,333,004 B1
(45) Date of Patent: Dec. 25, 2001

(54) APPARATUS AND METHOD FOR REMOVING MICROBIAL CONTAMINANTS FROM A FLOWING FLUID

(76) Inventor: Dan M. Sheldon, 21310 SW. Wildflower Dr., Newberg, OR (US) 97132

(*) Notice: Subject to any disclaimer, the term of this patent is extended or adjusted under 35 U.S.C. 154(b) by 0 days.

(21) Appl. No.: 09/479,959

(22) Filed: Jan. 10, 2000

(51) Int. Cl.[7] ................................. A61L 9/00; B01L 1/00
(52) U.S. Cl. ......................... 422/4; 422/122; 435/303.1; 435/809
(58) Field of Search ................................ 435/266, 289.1, 435/303.1, 809; 422/4, 122, 123, 104

(56) References Cited

U.S. PATENT DOCUMENTS

| | | |
|---|---|---|
| 3,002,895 | 10/1961 | Freedman . |
| 3,576,721 | 4/1971 | Mason . |
| 3,887,436 | 6/1975 | Haddad et al. . |
| 3,929,584 | 12/1975 | Mansfield . |
| 3,948,732 | 4/1976 | Haddad et al. . |
| 4,033,825 | 7/1977 | Haddad et al. . |
| 4,039,775 | 8/1977 | Andra . |
| 4,336,329 | 6/1982 | Hesse et al. . |
| 4,356,967 | 11/1982 | Lunick . |
| 4,621,647 * | 11/1986 | Loveland . |
| 4,668,854 | 5/1987 | Swan . |
| 4,684,510 * | 8/1987 | Harkins . |
| 4,689,303 | 8/1987 | Kraft et al. . |
| 4,701,415 | 10/1987 | Dutton et al. . |
| 5,090,617 | 2/1992 | Swan et al. . |
| 5,169,217 | 12/1992 | Orchard et al. . |
| 5,352,414 | 10/1994 | Rothenburg . |
| 5,415,770 * | 5/1995 | Heskett . |
| 5,792,427 * | 8/1998 | Hugh et al. . |
| 6,013,119 * | 1/2000 | Cecchi et al. . |
| 6,117,687 | 9/2000 | Hugh . |

FOREIGN PATENT DOCUMENTS

| | | |
|---|---|---|
| 8-71340-A * | 8/1996 | (JP) . |
| 10-234351-A * | 10/1998 | (JP) . |

OTHER PUBLICATIONS

"Waterjacketed $CO_2$ Incubators, Models 1815TC, 1825TC, 1845TC, Sheldon Manufacturing, Inc.," Mar. 1990.

Lucille A. Ouellette, "Control and Prevention of Contamination in Cell Culture Incubators," date unknown.

Full Size Water–Jacketed Incubators, Ultima and Elite Series, Revco Catalogue, www.revco–sci.com, Oct. 19, 1999.

"Waterjacketed $CO_2$ Incubators, Models 1815TC, 1825TC, 1845TC, Installation and Operating Instructions," Sep. 15, 1988.

\* cited by examiner

*Primary Examiner*—William H. Beisner
(74) *Attorney, Agent, or Firm*—Kolisch Hartwell Dickinson McCormack & Heuser

(57) ABSTRACT

A cell culture incubator comprising a chamber, an airflow passage through which fluids may recirculate through the chamber, a filter disposed within the airflow passage, and a structural component constructed of a material with antimicrobial properties. The structural component is disposed in the airflow passage so that microbial contaminants in air flowing into or within the incubator will contact the antimicrobial structural component and be retained in a portion of the airflow passage. The portion of the airflow passage in which the microbial contaminants are retained may be adjacent to the structural element.

25 Claims, 3 Drawing Sheets

APPARATUS AND METHOD FOR REMOVING MICROBIAL CONTAMINANTS FROM A FLOWING FLUID

BACKGROUND OF THE INVENTION

The present invention relates to an air filter that includes a structural component made of a material with anti-microbial properties. More particularly, the invention relates to an air intake filter for a cell culture incubator that includes a structural component that inhibits the reproduction of microbial contaminants and traps them away from the chamber of the incubator.

The use of cell cultures is a tremendously popular research tool in a variety of scientific disciplines. It involves the in vitro growth of cells in a cell culture incubator, for example a humidified $CO_2$ incubator. The popularity of the technique has lead to many advances in cell growth techniques and equipment, which have made the growth of cell cultures more reliable and reproducible. However, some problems associated with cell culture exist despite the many recent advances made in the field. One of the most prevalent of these problems is contamination.

Many sources exist for the contamination of cell cultures. For example, any piece of equipment that a cell culture may encounter, such as an autoclave, fume hood or incubator, may introduce contaminants into the culture. Humidified $CO_2$ cell culture incubators are designed to provide a suitable environment for the growth of cells in culture. The primary functional components of these incubators include a chamber in which the cultures are placed for growth, a blower to circulate air in the chamber, a heating system to heat the chamber to an optimal cell growth temperature, and a filter to remove particulate contaminants from the chamber. Additionally, some incubators may include a water pan in the bottom of the chamber to humidify the cell growth environment or a $CO_2$ input system to vary the makeup of the atmosphere inside the incubator. The resulting warm, moist and dark environment is perfect for the growth of cell cultures. It is also perfect for the growth of bacteria, mold, yeast and fungi contaminants.

Contamination can cause several types of problems in a cell culture incubator. For example, if contaminants infect a cell culture, it may ruin the culture and any experiment relying on that culture. Also, contaminants may grow in the humidity pan. The relative humidity inside an incubator is a function of the evaporation rate of water from the humidity pan. The rate of evaporation is dependent upon the surface area of the pan and the surface tension of the liquid in the pan. If contaminants grow in the pan, they can alter the surface tension of the water and upset the humidity characteristics of the chamber.

To prevent the contamination of a cell culture incubator, the incubator must be cleaned at regular intervals using a rigorous procedure. Even with regular cleaning, however, some locations in the incubator are particularly susceptible to contamination. One of these is the air filter. The air filter in an incubator is generally mounted on an interior surface of the chamber. The blower draws air through the filter, where the air is cleaned of particulate contaminants. Upon leaving the filter, the air flows through a conduit back into the incubator chamber, and is again cycled through the filter. One source of the contaminants removed by the filter is the opening of the chamber door by laboratory personnel. Microbial contaminants, such as bacteria and spores, enter the incubator chamber with each opening of the door. These contaminants are then drawn into the filter by the circulating air and trapped. They may then grow in the filter. Once the filter is contaminated, the potential exists for samples in the chamber to be contaminated as well.

Antibiotics may be added to cell cultures to prevent the contamination of a sample by a contaminated incubator, but they are generally not recommended for use in samples, with limited exceptions. Most antibiotics do not kill the bacteria, but only slow its growth, and thus do not remove the contaminant from the chamber. Also, the long-term use of antibiotics may alter the cultures grown in the incubator, resulting in the selective growth of antibiotic-resistant strains of cells over non-resistant strains. Furthermore, the antibiotic may be toxic to the cultured cells as well. For these reasons, it is not desirable to use an antibiotic in the cell culture to control contamination.

Some materials are known to inhibit the growth of bacteria and other microbial contaminants while showing no toxicity toward eukaryotic cells that are commonly cultured in incubators. Copper and some of its salts and oxides are among these materials. Copper compounds have long been used to control such organisms as algae, mollusks, fungi, and bacteria. Copper sulfate, for example, has many uses in agriculture. It finds its primary use in the control of fungal diseases of plants, but is also used against crop storage rots, for the control and prevention of certain animal diseases such as foot rot, and for the correction of copper deficiency in soils and animals. It also has anti-microbial uses outside of agriculture. For instance, it may be added to reservoirs to prevent the development of algae in potable water supplies. Copper sulfate, however, is not the only copper compound with antifungal and antibacterial applications. Other copper compounds, such as cuprous oxide ($Cu_2O$) and copper acetate ($CuCH_2COOH$), have also been used as fungicides. Despite its heavy use in agriculture and industry, however, neither copper nor most of its compounds commonly used in these applications have ever been shown to be toxic or to cause any occupational diseases.

Incubators have been constructed with copper chambers in the past to take advantage of the anti-microbial properties of copper compounds. For instance, Revco currently manufactures an incubator with a copper bonded interior surface, the Revco ULTIMA incubator, described in their online catalog at the following website:

http://www.revco-sci.com/catalog/incubators/ultima elite.htm.

It is also available through Fisher Scientific (1994 Fischer Scientific Catalog, p. 1109). The bonded copper interior surface is effective to inhibit the growth of many contaminants. However, contaminants that enter the chamber when the door is opened may still grow in areas not protected by the copper surface, such as the blower, the filter or other components. Moreover, if the filter becomes infected, the blower can spread contaminants from the filter to all other parts of the chamber. The possibility thus exists that some of these contaminants which have grown in the filter and not encountered the copper interior surface may infect cultures in the chamber.

Thus, problems exist both in inhibiting the growth of microbial contaminants in the filter of a cell culture incubator, and in segregating and retaining the inhibited contaminants away from the chamber.

SUMMARY OF THE INVENTION

One aspect of the present invention provides a cell culture incubator comprising a chamber, an airflow passage through which fluids may recirculate through the chamber, a filter disposed within the airflow passage, and a structural component constructed of a material with anti-microbial properties. The structural component is disposed in the airflow passage so that microbial contaminants in air flowing into or within the incubator will contact the anti-microbial structural component and be retained in a portion of the airflow passage. The portion of the airflow passage in which the microbial contaminants are retained may be adjacent to the structural element.

Another aspect of the present invention provides an air filter for removing microbial contaminants from air, comprising a casing, a filter element, and a structural element made of a material with anti-microbial properties. The casing defines a passage for airflow through the filter. The filter element is disposed in the casing such that air must flow through the filter element to flow through the passage. The structural element made of a material with anti-microbial properties is disposed in the casing such that air must flow through the structural element before flowing into the incubator.

Another aspect of the present invention provides an anti-microbial structural element for use in an air intake filter, where the air filter includes a filter element. The structural component comprises a mesh of a material with anti-microbial properties, wherein the mesh may be configured such that all air flowing through the filter element must pass through the mesh.

Yet another aspect of the present invention provides a method of removing microbial contaminants from air, comprising (1) providing a structural component made of a material with anti-microbial properties in an air filter, the air filter including a filter element, wherein the structural component is located at a point upstream or downstream of the filter element; (2) creating an airflow though the filter element; (3) exposing microbial contaminants in air flowing through the filter element to the structural component made of a material with anti-microbial properties; and (4) trapping microbial contaminants in the filter element after exposing them to the structural component made of a material with anti-microbial properties. Referring to (3), the structural component may take the form of a device capable of killing microbial contaminants. That device could be an electrified gradient of wires or other elements, a microwave emission source, or other radiation-emitting devices.

DETAILED DESCRIPTION OF THE PREFERRED EMBODIMENTS

Figure 1:
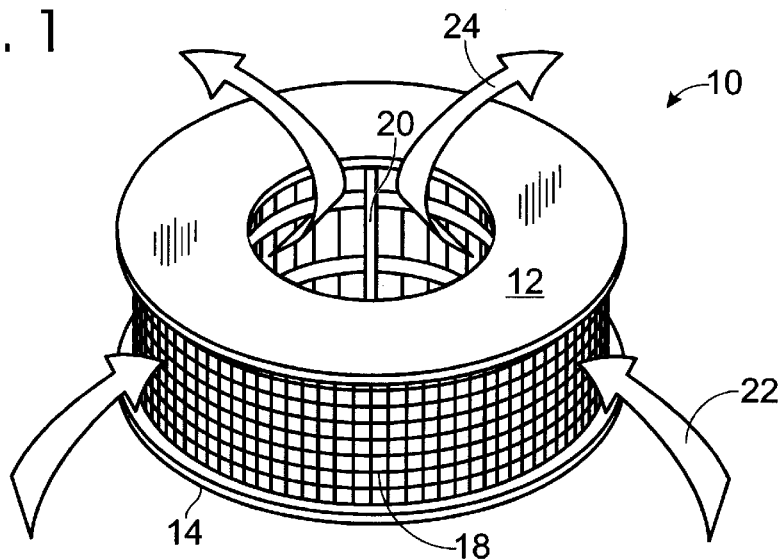
FIG. 1 is an isometric view of a filter according to a first embodiment of the present invention.
Figure 2:
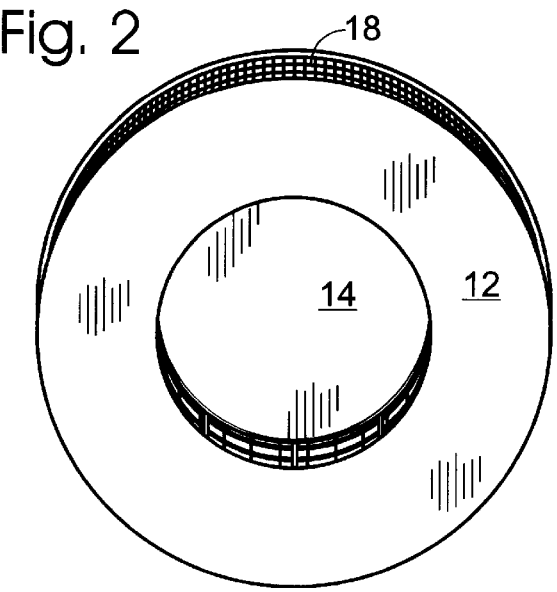
FIG. 2 is a top plan view of the filter of the embodiment of FIG. 1.

The present invention provides an apparatus and a method for removing microbial contaminants from a flowing fluid. The method is particularly suited for application in a cell culture incubator. FIG. 1 shows generally a schematic of an apparatus that may be used to practice the present invention. A filter is indicated at 10. The filter has an upper piece 12 and a lower piece 14. Upper piece 12 defines a hole in its center portion, while lower piece 14 is solid, as shown in FIG. 2, forcing air to flow out of filter 10 through the hole in upper piece 12. A filter element 16 is disposed between the upper piece and lower piece. The filter element is held in place by a mesh 18 surrounding the filter element on one side and a bracket 20 on the other side. Airflow, indicated at 22 and 24, passes through filter 10 by first passing through mesh 18, through filter element 16, and out of the hole defined by top piece 12. Top piece 12 and bottom piece 14 are joined together by mesh 18, with one edge of mesh 18 bonded to top piece 12 and the other to bottom piece 14.

Figure 3:
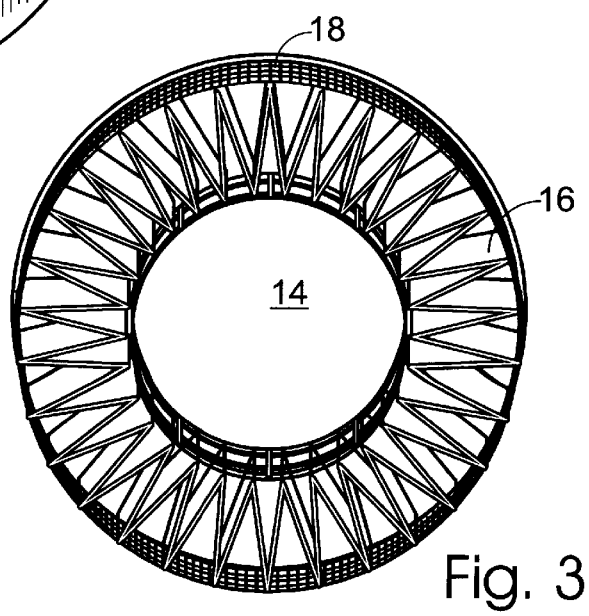
FIG. 3 is a top plan view of the filter of the embodiment of FIG. 1 with the top piece removed.

FIG. 3 shows a view of the top of filter 10 with top piece 12 removed. Filter element 16 can be seen in this view to be configured in a zig-zag pattern to maximize its surface area. This maximizes the speed of airflow through the filter because the total surface area of the pores for air to pass through is maximized. This also maximizes the life of the filter, as a larger surface area will clog with particulate less quickly than a smaller surface area.

According to the present invention, one of the structural components of an embodiment of the invention is constructed of a material with anti-microbial properties. While many materials, both solid and liquid, may be used for the structural component of the present invention, copper is a preferred material. When elemental copper metal is exposed to air, it reacts with various chemical compounds present in the air to form a variety of copper salts and oxides. For instance, in the presence of sulfur oxides, copper will form copper sulfide. In the presence of oxygen, the copper will oxidize over a period of time to $Cu_2O$ and $CuO$. These compounds will generally form as a surface layer on the elemental copper metal. Additionally, water-soluble copper compounds such as copper sulfate may exist as an aqueous phase if there is any water present on the surface of the copper. Both a surface layer and an aqueous layer of the anti-microbial copper compounds will be present on any copper in the warm, moist environment of the incubator interior. The presence of these compounds on the surface of a structural element made of copper will prevent bacteria, fungi, algae, and other contaminants from growing on the element.

In one embodiment of this invention, mesh 18 may be made of copper. Mesh 18 is shown separate from the rest of filter 10 in FIG. 4. Mesh 18 includes both vertical members 26 and horizontal members 28. Mesh 18 is configured to completely surround filter element 16 with no gaps. Thus, according to the embodiment of the invention shown in FIG. 1, mesh 18 will be the cylindrical shape shown in FIG. 4. The size of the gaps defined by vertical members 26 and horizontal members 28 may be chosen to suit any particular filter or chamber design to accommodate particular airflow characteristics.

Figure 4:
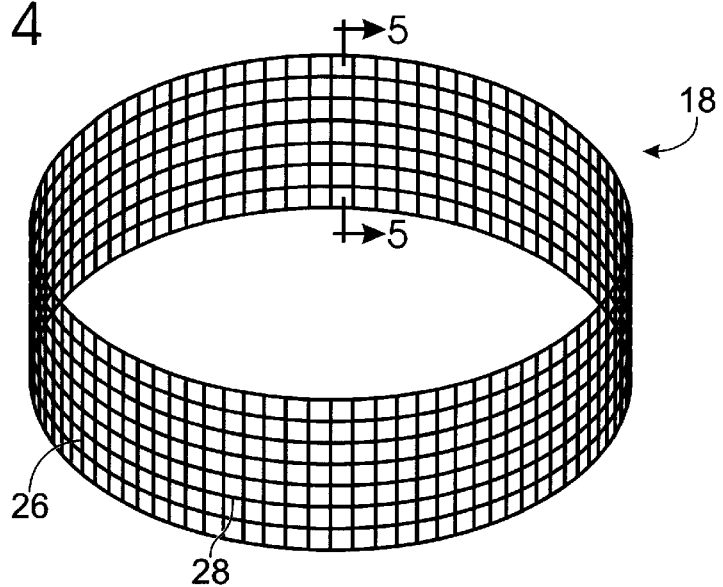
FIG. 4 is an isometric view of an anti-microbial mesh according to the first embodiment of the present invention.
Figure 5:
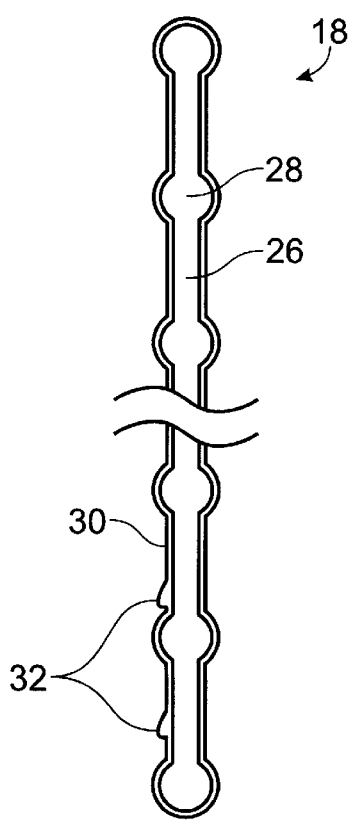
FIG. 5 is a sectional view taken along line 5—5 of FIG. 4.
Figure 6:
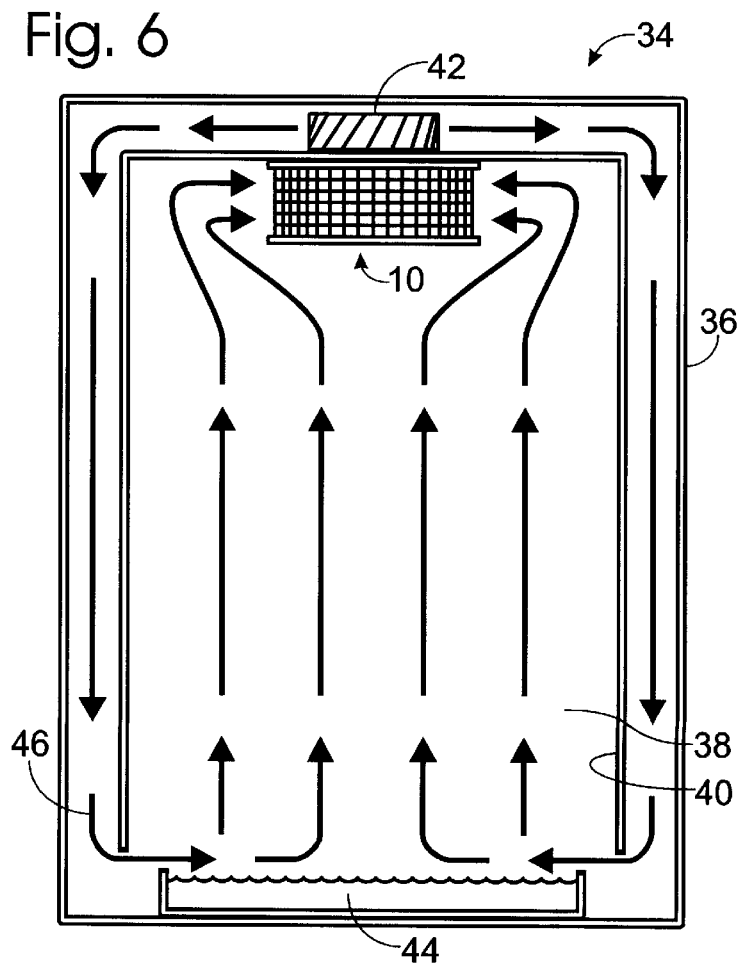
FIG. 6 is a sectional view of an incubator showing airflow through a filter according to the present invention.
Figure 8:
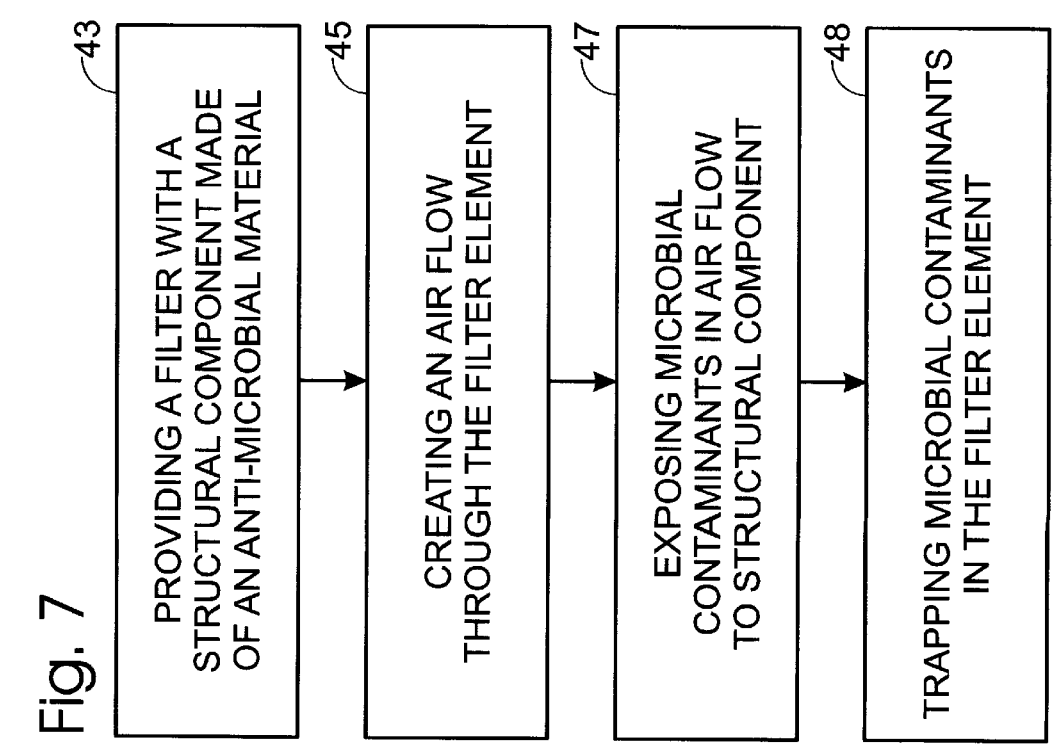
FIG. 8 is a flow diagram depicting a method of removing microbial contaminants from a flowing gas according to another embodiment of the present invention.
Figure 7:
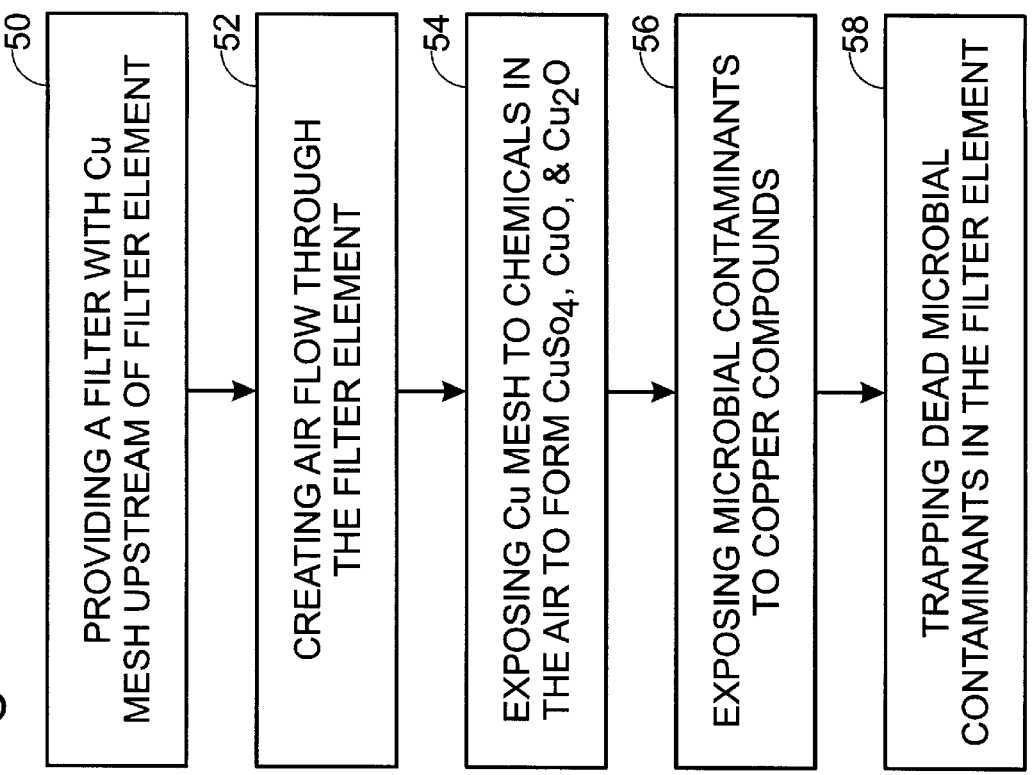
FIG. 7 is a flow diagram depicting a method of removing microbial contaminants from a flowing gas according to an embodiment of the present invention.

FIG. 5 shows a sectional view of the mesh taken along line 5—5 of FIG. 4. Though FIG. 5 demonstrates the surface condition of a mesh in a humidified incubator environment, the mesh will show anti-microbial properties in any incubator—humidified or not. The view is taken as a cross-section slightly off the center of a vertical member 26, and the horizontal members 28 appear as nodes along vertical member 26. A thin surface layer 30 covers all exposed surfaces of mesh 18. Surface layer 30 is a solid layer of various copper compounds formed in the reactions between copper and chemicals present in the air inside the incubator chamber. Among the compounds present in layer 30 will be many of the copper compounds that exhibit anti-microbial properties. Due to the moist environment inside the incubator, there may be some moisture 32 present on the surface of mesh 18. Though droplets of moisture 32 are shown only in two places on mesh 18 in FIG. 3 for reasons of clarity, in reality moisture 32 may be found covering the entire surface, or any fraction of the surface, of mesh 18. Any water-soluble copper compounds present in surface layer 30 will be found as an aqueous phase in moisture 32.

Microbial contaminants encountering surface layer 30 or moisture 32 will be inhibited from proliferating by the compounds present in layer 30 and moisture 32. Furthermore, moisture 32 may drip down mesh 18 and into the bottom of the filter, defined by bottom piece 14. Bottom piece 14 is solid, and will hold any moisture that drips off of mesh 18. The moisture may spread across the surface of bottom piece 14, and may encounter the bottom edge of filter element 16. Filter element 16 is often made of a material such as filter paper that may absorb moisture. Moisture may be drawn up into filter element 16 from the surface of bottom piece 14 by capillary action, and impregnate filter element 16 with any aqueous copper compounds present in moisture 32. The anti-microbial compounds may spread from mesh 18 to other parts of filter 10, inhibiting the growth of contaminants throughout filter 10. Furthermore, any contaminants that are drawn into the filter will remain in the filter, trapped by filter element 16. The contaminants will remain in contact with the anti-microbial compounds present in both mesh 18 and filter element 16, and will not contaminate the filter. Finally, the contaminants will not fall out of filter 10 back into the chamber, as the direction of airflow from the chamber into filter 10 will hold the contaminants inside of filter 10. In a non-humidified incubator, surface layer 30 of various copper compounds will still be present, but less moisture will be present on the surface of mesh 18. In another embodiment of the present invention, the structural element may take the form of filter element 16 impregnated with the anti-microbial compounds.

FIG. 6 depicts the use of filter 10 in an incubator. An incubator is indicated generally at 34. Incubator 34 includes a casing 36, a chamber 38, an interior surface 40, a blower 42, an optional water pan 44, and filter 10. The incubator will also include a heating unit, which is not depicted in this figure. Arrows 46 indicate the direction of airflow in the incubator. Air is continuously circulated through filter 10, out blower 42, through the incubator casing 36, and back into chamber 40 at the bottom of the chamber, where it is again drawn upward toward filter 10. When the door to chamber 40 is opened to insert or remove a sample from chamber 40, contaminants present in the air, on any tools inserted into the chamber, or on the laboratory personnel using the incubator may be introduced into chamber 40. These contaminants may be drawn into filter 10 by the upward air currents created by blower 42. Upon entering filter 10, the contaminants will encounter anti-microbial mesh 18 and filter element 16. Thus, the contaminants will be trapped in filter element 16 and the copper compounds generated at mesh 18 will inhibit their reproduction.

Another aspect of the present invention provides a method of removing microbial contaminants from air. The method is suited for use in any application where a sterile, microbe-free environment is desired, such as in humidified $CO_2$ cell culture incubator. One embodiment of this aspect is shown in FIG. 7. First, a filter is provided at 43. According to this embodiment, the filter will have a structural component made of an anti-microbial material, and will also have a filter element. Next, a flow of air is created through the filter at 45. The flow of air will bring any microbial contaminants present in the air into contact with the anti-microbial material of the structural component, and will expose the contaminants to the anti-microbial structural component at 47. Finally, after exposing the contaminants to the anti-microbial material, the contaminants are trapped in the filter element at 48 and thus removed from the airflow. The air downstream of the filter will be contaminant free.

Another embodiment of this aspect of the present invention is shown in FIG. 8, which illustrates the removal of microbial contaminants from the air in a cell culture incubator. In this application, a copper mesh is provided in a cell culture incubator filter in a location upstream of the filter element at 50. Next, a flow of air is created through the filter at 52. The airflow can be created by a blower, or by any suitable pumping method. Exposure of the mesh to the warm, moist, $CO_2$ rich air inside the incubator will result at 54 in the formation of different copper compounds, such as $CuSO_4$ and $Cu_2O$, that may display anti-microbial properties. Any microbial contaminants in the incubator will be drawn into the filter and exposed to the copper compounds at 56. Finally, the microbial contaminants will be trapped in the filter element at 58, where they will be prevented from reproducing by the presence of the copper compounds.

While the invention has been disclosed in its preferred form, the specific embodiments thereof as disclosed and illustrated herein are not to be considered in a limiting sense as numerous variations are possible. Applicants regard the subject matter of their invention to include all novel and non-obvious combinations and subcombinations of the various elements, features, functions and/or properties disclosed herein. No single feature, function, element or property of the disclosed embodiments is essential to all embodiments. The following claims define certain combinations and subcombinations which are regarded as novel and non-obvious. Other combinations and subcombinations of features, functions, elements and/or properties may be claimed through amendment of the present claims or presentation of new claims in this or a related application. Such claims, whether they are different, broader, narrower or equal in scope to the original claims, are also regarded as included within the subject matter of applicants' invention.

What is claimed is:

1. A cell culture incubator, comprising:

a chamber;

an airflow passage through which gasses may recirculate in and out of the chamber;

a filter disposed within the airflow passage, the filter having a filter element;

and a structural component constructed of a material with anti-microbial properties, wherein the structural component is disposed within the filter upstream of the filter element so that microbial contaminants in air flowing into the incubator will contact the structural component and then be retained in the filter element.

2. The incubator of claim 1 wherein the structural component is made of copper.

3. The incubator of claim 1, wherein the filter includes a casing, and wherein the structural component is disposed inside the casing.

4. The incubator of claim 1, wherein the structural component is a mesh.

5. The incubator of claim 1, wherein the material with anti-microbial properties may react with chemical compounds in the air to form products with anti-microbial properties.

6. The incubator of claim 5, wherein the material with anti-microbial properties is copper, wherein the chemical compounds in the air include sulfur oxides, and wherein the products with anti-microbial properties include copper sulfate.

7. The incubator of claim 5, wherein the material with anti-microbial properties is copper, wherein the chemical compounds in the air include oxygen, and wherein the products with anti-microbial properties include copper oxides.

8. An incubator including a chamber, an airflow passage for recirculating a gas into and out of the chamber, and a filter configured to filter air circulated through the airflow passage, the filter comprising:

a casing, the casing defining a passage for airflow through the filter;

a filter element disposed in the casing such that air must flow through the filter element to flow through the passage; and a structural element made of a material with anti-microbial properties disposed in the casing upstream of the filter element.

9. The filter of claim 8, wherein the structural component is a mesh.

10. The filter of claim 8, wherein the material with anti-microbial properties is copper.

11. The filter of claim 8, wherein the material with anti-microbial properties may react with chemical compounds in the air to form products with anti-microbial properties.

12. The filter of claim 11, wherein the material with anti-microbial properties is copper, wherein the chemical compounds in the air include sulfur oxides, and wherein the products with anti-microbial properties include copper sulfate.

13. The filter of claim 11, wherein the material with anti-microbial properties is copper, wherein the chemical compounds in the air include oxygen, and wherein the products with anti-microbial properties include copper oxides.

14. A method of removing microbial contaminants from an incubator chamber, comprising:

providing an air filter having a structural component made of a material with anti-microbial properties, the air filter also including a filter element;

creating an airflow though the filter element;

exposing microbial contaminants in air flowing through the filter element to the structural component made of a material with anti-microbial properties; and trapping microbial contaminants in the filter element after exposing the microbial contaminants to the structural component.

15. The method of claim 14, wherein providing a structural component made of a material with anti-microbial properties includes providing a mesh made of a material with anti-microbial properties.

16. The method of claim 14, wherein providing a structural component made of a material with anti-microbial properties includes providing a structural component made of a material that may react with chemical compounds in air to form products with anti-microbial properties.

17. The method of claim 16, further comprising exposing the structural element to air before exposing microbial contaminants in the air to the structural component so that the structural component reacts with chemical compounds in the air to form products with anti-microbial properties.

18. The method of claim 17, wherein the material that may react with chemical compounds in air is copper, wherein the chemical compounds in air include sulfur oxides, and wherein the products include copper sulfate.

19. The method of claim 17, wherein the material that may react with chemical compounds in air is copper, wherein the chemical compounds in air include oxygen, and wherein the products include copper oxides.

20. A cell culture incubator, comprising:

a chamber;

an airflow passage; and a filter configured to filter air circulated through the airflow passage, wherein the filter includes an inlet, an outlet, an anti-microbial structural component disposed between the inlet and the outlet, and a filter element configured to trap microbial contaminants exposed to the anti-microbial structural component.

21. The cell culture incubator of claim 20, wherein the filter element is disposed downstream of the anti-microbial structural component.

22. The structural component of claim 20, wherein the material with anti-microbial properties is copper.

23. The structural component of claim 20, wherein the material with anti-microbial properties may react with chemical compounds in the air to form products with anti-microbial properties.

24. The structural component of claim 23, wherein the material with anti-microbial properties is copper, wherein the chemical compounds in the air include sulfur oxides, and wherein the products with anti-microbial properties include copper sulfate.

25. The structural component of claim 23, wherein the material with anti-microbial properties is copper, wherein the chemical compounds in the air include oxygen, and wherein the products with anti-microbial properties include copper oxides.

* * * * *